United States Patent
Yokoyama et al.

(12)

(10) Patent No.: US 7,544,821 B2
(45) Date of Patent: Jun. 9, 2009

(54) α-KETOL UNSATURATED FATTY ACID DERIVATIVE AND PLANT GROWTH REGULATING AGENT USING SAME (75) Inventors: Mineyuki Yokoyama, Yokohama (JP); Shoko Yamaguchi, Yokohama (JP); Satoshi Watanabe, Tokyo (JP)

(73) Assignees: Shiseido Company, Ltd., Tokyo (JP); Kumiai Chemical Industry Co., Ltd., Tokyo (JP)

( * ) Notice: Subject to any disclaimer, the term of this patent is extended or adjusted under 35 U.S.C. 154(b) by 214 days.

(21) Appl. No.: 11/667,687

(22) PCT Filed: Nov. 25, 2005

(86) PCT No.: PCT/JP2005/022130

§ 371 (c)(1),
(2), (4) Date: May 14, 2007

(87) PCT Pub. No.: WO2006/057446

PCT Pub. Date: Jun. 1, 2006

(65) Prior Publication Data

US 2009/0076309 A1 Mar. 19, 2009

(30) Foreign Application Priority Data

Nov. 25, 2004 (JP) ............................. 2004-340818

(51) Int. Cl.
*C07C 59/147* (2006.01)
*C07C 59/00* (2006.01)
*A01N 65/00* (2009.01)
*A01N 37/00* (2006.01)

(52) U.S. Cl. ..................... 554/115; 562/577; 562/579; 504/189; 504/320

(58) Field of Classification Search ................ None
See application file for complete search history.

(56) References Cited

U.S. PATENT DOCUMENTS 6,057,157 A * 5/2000 Yokoyama et al. .......... 435/430
6,174,712 B1 * 1/2001 Yokoyama et al. .......... 435/136

FOREIGN PATENT DOCUMENTS

| EP | 0 823 994 A1 | 2/1998 |
| JP | 9-295908 | 11/1997 |
| JP | 10-324602 | 12/1998 |
| JP | 11-29410 | 2/1999 |
| JP | 2002-226309 | 8/2002 |
| WO | WO 97/32478 | 9/1997 |

OTHER PUBLICATIONS

Yokoyama, Mineyuki et al., "Stress-Induced Factor Involved in Flower Formation of *Lemna* is an α-Ketol Derivative of Linolenic Acid", *Plant Cell Physiol.*, 2000, pp. 110-113, vol. 41.

* cited by examiner

*Primary Examiner*—Sikarl A Witherspoon
(74) *Attorney, Agent, or Firm*—Foley & Lardner LLP (57) ABSTRACT

α-Ketol unsaturated fatty acid derivatives represented by the general formula (1); and plant growth regulators containing the same, which develop plant growth regulation performance such as flower bud formation acceleration in low concentrations and are excellent in stability: wherein $R^1$ is straight-chain $C_{1-5}$ alkyl or a straight-chain unsaturated $C_{3-5}$ hydrocarbon group having one or two double bonds; and $R^2$ is straight-chain $C_{1-15}$ alkylene or a straight-chain unsaturated $C_{2-15}$ hydrocarbon chain having one to three double bonds, with the proviso that the number of carbon-carbon double bonds is at most four.

5 Claims, 3 Drawing Sheets

α-KETOL UNSATURATED FATTY ACID DERIVATIVE AND PLANT GROWTH REGULATING AGENT USING SAME

This is a 371 of PCT/JP2005/022130 filed Nov. 25, 2005 and published as WO 2006/057446 on Jun. 1, 2006.

TECHNICAL FIELD

The present invention relates to an α-ketol unsaturated fatty acid derivative and a plant growth regulating agent which utilizes the properties possessed by that compound. More specifically, the present invention relates to a novel substance, that is, an α-ketol unsaturated fatty acid derivative, a plant flower budding promoting agent and plant activating agent containing the same, and an application including the same, that is, a plant growth regulating agent, particularly preferably relates to a plant flower budding promoting agent.

BACKGROUND ART

[Prior Art Documents]
[Patent Document 1] Japanese Patent Publication (A) No. 09-295908
[Patent Document 2] Japanese Patent Publication (A) No. 11-029410
[Patent Document 3] Japanese Patent Publication (A) No. 2002-226309
[Non-Patent Document 1] Yokoyama et al., Plant Cell Physiol., 41, 110-113, 2000.

Plant growth regulation, in particular the development of technology to promote flower budding in plants, is extremely important in improving the efficiency of supply of farm crops and garden plants. As factors determining flower budding in plants, the day length, low temperatures, plant aging, etc. are known. In plants, the parts sensitive to the day length are the leaf blades. Flower budding occurs at the growth points. It has been learned that some sort of signal is sent from the leaf blade through the stalk and stem to the growth point, whereby the flower budding is started. This signal is generally called a "florigen". If it were possible to isolate and identify the florigen, it would be possible to artificially regulate the blooming timing of plants, without regard as to the day length. This would have a tremendous effect to many fields where plants are involved.

Therefore, in the past, attempts have been made to artificially adjust the blooming timing by clarifying more the mechanism of flower budding of plants. For example, if administering gibberellin, one growth hormone of a plant, it is learned that flower budding occurs easily in several plants. In addition, it is learned that, in pineapples, blooming occurs by administering one type of synthetic auxin, that is, α-naphthalene acetic acid. This is actually utilized industrially.

Although the situation is as explained above, the effects of these plant hormones are limited. Further advances in blooming techniques, specifically, the isolation and identification of substances directly involved in flower budding and the establishment of a blooming technique using such substances, are desired.

From the above-mentioned situation, the present inventors engaged in intensive studies and, as a result, found that an α-ketol unsaturated fatty acid having the specific structure of the following general formula (2A) acts alone, or in combination with norepinepherine, one kind of catechol amine, to activate the desired flower budding inducing action for a wide variety of plants (see Patent Documents 1 and 2).

Further, thereafter, the inventors engaged in further studies and found that an α-ketol unsaturated fatty acid amide obtained by amide-bonding an amino acid to the carboxyl group of the above-mentioned α-ketol unsaturated fatty acid has a similar activity at a lower concentration (see Patent Document 3).

Formula (2A)

DISCLOSURE OF THE INVENTION

However, if considering reducing the cost of production of this α-ketol unsaturated fatty acid amide or the amount given to a plant, a compound exhibiting a similar effect at a lower concentration is desired.

Further, the α-ketol unsaturated fatty acid having the formula (2A) and the α-ketol unsaturated fatty acid amide are easily decomposed and, therefore, the development of a stabler substance having plant growth regulation properties such as plant flower budding promotion and plant activation has been desired.

Therefore, the inventors engaged in research and development with the object of solving the above problems and, as a result, found that, surprisingly, if synthesizing a novel substance of a specific structure having both an α-ketol and an olefin structure and also having a diol structure in which an OH group is present at the two adjacent carbons, that is, having an adjacent diol structure, that is, the α-ketol unsaturated fatty acid derivative (1) having the following general formula (1), and, when the substance is applied to a plant, there is a plant growth regulation properties.

That is, the inventors found that, if a novel substance having α-ketol, cis double bonds, and an adjacent diol structure, that is, the following α-ketol unsaturated fatty acid derivative (1) is synthesized and applied to a plant, plant growth regulation properties, especially the promotion of flower budding at a far lower concentration can be obtained.

Further, the inventors studied a method for producing the α-ketol unsaturated fatty acid derivative (1) and succeeded in the development of an inexpensive production method thereof.

Furthermore, the inventors found that this compound is difficult to break down and is superior in stability.

Consequently, the present invention has, as the problem to be solved by the invention, that is, as the object of the invention, the provision of novel substance having a plant growth regulation performance, that is, an α-ketol unsaturated fatty acid derivative (1), and a plant flower budding promoting agent or other plant growth regulator containing the same.

The present invention, as explained above, provides a novel substance having a plant growth regulation property, that is, the α-ketol unsaturated fatty acid derivative (1), and plant growth regulating agent containing the same such as a plant flower budding promoting agent. The former α-ketol unsaturated fatty acid derivative (1) is represented by the following general formula (1).

The latter plant growth regulating agent contains the α-ketol unsaturated fatty acid derivative (1) represented by the following general formula (1). This can be particularly preferably used, as a plant flower budding promoting agent.

Formula (1)

wherein $R_1$ indicates a $C_1$ to $C_5$ straight chain alkyl group or $C_3$ to $C_5$ straight chain unsaturated hydrocarbon group having one or two double bonds, $R_2$ indicates a $C_1$ to $C_{15}$ straight chain alkylene or $C_2$ to $C_{15}$ straight chain unsaturated hydrocarbon chain having one to three double bonds, where the number of double bonds between carbons is a maximum of 4.

Note that the "straight chain" in the straight chain alkyl group, straight chain unsaturated hydrocarbon group, straight chain alkylene and straight chain unsaturated hydrocarbon chain means the chain of carbons are bonded on a straight, line without branching. For example, a "straight chain alkylene" is a divalent group of atoms produced by removing the two hydrogen atoms bonded to two different carbon atoms in a aliphatic hydrocarbon composed of a chain of carbons bonded on a straight line, without branching, and is represented by the general formula —$(CH_2)_n$—.

The present invention provides a novel substance having both an α-ketol and an olefin structure and, in addition thereto, having an adjacent diol structure which has plant flower budding promotion property or other plant growth regulation ability, that is, an α-ketol unsaturated fatty acid derivative (1), and provides a plant flower budding promoting agent and plant activating agent utilizing their performance and a plant growth regulating agent including the same.

Further, as a plant activating agent, the α-ketol unsaturated fatty acid derivative (1) has the properties of breaking dormancy, promoting rooting, promoting blooming, promoting flowering, promoting grass-stalk growth, and the like. Therefore, by utilizing these properties, it is possible to specifically utilize the activator, as a dormancy breaking agent, rooting agent, blooming promoting agent, flowering promoting agent, grass-stalk growth promoting agent, etc.

Further, this compound can exhibit these properties at a lower concentration, is difficult to be decomposed, and is more superior in the stability. It is therefore possible to provide a superior flower budding promoting agent, plant activating agent, and a plant growth regulating agent.

BRIEF DESCRIPTION OF THE DRAWINGS

The present invention will now be explained with reference to the drawings.

BEST MODE FOR CARRYING OUT THE INVENTION

The present invention will now be explained in detail with reference to embodiments of the present invention including the best mode for carrying out the invention.

The α-ketol unsaturated fatty acid derivative of the present invention is represented by the general formula (1) and can be utilized, as a plant flower budding promoting agent or a plant growth regulating agent including applications of a plant activating agent and the like, realizing the breaking dormancy, promoting rooting, promoting blooming, promoting flowering, promoting grass-stalk growth, and other property.

A derivative of the present invention can express property suitable for the above applications so long as it has the structure of the above general formula (1).

The derivative of the present invention specifically is one wherein in the above general formula (1), $R_1$ indicates a $C_1$ to $C_5$ straight chain alkyl group or a $C_3$ to $C_5$ straight chain unsaturated hydrocarbon group having one or two double bonds. In addition, $R_2$ indicates a $C_1$ to $C_{15}$ straight chain alkylene or $C_2$ to $C_{15}$ straight chain unsaturated hydrocarbon chain having one to three double bonds. The maximum number of double bonds between carbons is four. Because of the above, the above unsaturated fatty acid derivative of the present invention has 11 to 29 carbon atoms.

Specifically, the 9,15,16-trihydroxy-10-oxo-12 (Z)-octadecenoic acid represented by the following general formula (1A) is a preferable compound in the above general formula (1) and is suitable for the above applications. Note that the compound of the following general formula (1A) is a compound of the above general formula (1), in which $R_1$ is a $C_2$ straight chain alkyl group, and $R_2$ is a $C_7$ straight chain alkylene.

In addition, "Z" in the above chemical formula means the cis form in cis-trans isomerism, while the underline attached thereto shows that it should inherently be expressed by italics.

Formula (1A)

A. Regarding Synthesis of α-Ketol Unsaturated Fatty Acid Derivative (1)

First, the method of production of the α-ketol unsaturated fatty acid having the following general formula (2) encompassing the α-ketol unsaturated fatty acid having the formula (2A) will be explained.

Formula (2)

wherein $R_1$ indicates a $C_1$ to $C_5$ straight chain alkyl group or a $C_3$ to $C_5$ straight chain unsaturated hydrocarbon group having one or two double bonds, $R_2$ indicates a $C_1$ to $C_{15}$ straight chain alkylene or a $C_2$ to $C_{15}$ straight chain unsaturated hydrocarbon chain having one to three double bonds, provided that the maximum number of the double bonds between carbons is four.

It is widely known that the α-ketol unsaturated fatty acid having the above formula (2A) encompassed by the α-ketol unsaturated fatty acid having the general formula (2) is included in natural substances and can be produced from such natural substances by extraction and purification.

In addition, this can be obtained by using an enzyme such as lipoxygenase, which is act on α-linolenic acid according to the fatty acid metabolic pathway in a plant body. The α-ketol unsaturated fatty acid can also be obtained using an ordinary known chemical synthesis method.

The α-ketol unsaturated fatty acid (2) having the above general formula (2) encompassing the α-ketol unsaturated fatty acid having the formula (2A) can also be produced by, for example, the method described in the above Patent Document 1, Patent Document 2 or Non-patent Document 1.

The next production of the α-ketol unsaturated fatty acid derivative (1) can be carried out by bringing the above α-ketol unsaturated fatty acid (2) into contact with a strong oxidizing agent which would generate activated oxygen or chlorine radicals.

Such a strong oxidizing agent includes, for example, sodium hypochlorite and chlorinated isocyanulic acid. The reaction thereof may be finished within 1 hour, preferably 30 minutes or less.

If the reaction time is more than the necessary time, there is an increased risk that the generated α-ketol unsaturated fatty acid derivative (1) will be again decomposed. Therefore, the important thing is the ratio of the presence of the α-ketol unsaturated fatty acid (2) and the oxidizing agent.

For example, in the case of sodium hypochlorite, the sodium hypochlorite should be present in an amount of 0.01 to 0.5 moles per 100 moles of α-ketol unsaturated fatty acid (2). The amount of sodium hypochlorite is greatly influenced by the purity of the α-ketol unsaturated fatty acid. In the case of a high degree of purity (i.e., the purity of 90% or more), the above region is sufficient, but in the case of a low purity, 0.01 to 10 moles is the rule. The reaction temperature thereof is not particularly limited, but is preferably under ice cooling to a room temperature. In addition, regarding the reaction solvent, there is no problem even if a solvent other than water coexists in an amount of 80% or less. For example, hydrous solvents such as methanol, ethanol, acetone, may be used, but preferably the reaction is performed in water.

The compound according to the present invention may be detected using a UV detector. This may be combined with HPLC (i.e., Nanospace (Shiseido Co., Ltd., Tokyo)) and the like to confirm the production of the compound according to the present invention.

Furthermore, for isolation and purification from the reaction solution of the compound according to the present invention, it is possible to use an ordinary known method. For example, extraction with a solvent or by column chromatography and the like can be used.

B. Regarding Plant Growth Regulating Action of α-Ketol Unsaturated Fatty Acid Derivative (1)

The upper limit of the dosage of the active ingredient of the plant growth regulating agent according to the present invention, that is, the α-ketol unsaturated fatty acid derivative (1), on plants is not particularly limited. Namely, even if a large amount of the α-ketol unsaturated fatty acid derivative (1) according to the plant growth regulating agent of the present invention is applied, almost no negative effect on the plant such as growth inhibition will be observed.

This means that, compared with the situation where if excessively administering the conventionally used plant hormone agent, the plant will be remarkably negatively affected and, therefore, special care must be given so as not to overly administer it at the time of use, the plant growth regulator of the present invention is remarkably superior.

In addition, the lower limit of the dosage of the α-ketol unsaturated fatty acid derivative (1) based upon the plant differs depending on the type or size of the plant specimen, but a concentration of 1 µM or so or more per dosage per single plant specimen is the general rule.

The amount of the α-ketol unsaturated fatty acid derivative (1) in the flower budding promoting agent of one aspect of the plant growth regulating agent of the present invention may be selected depending on the mode of use or the type of the plant covered by use or further the specific form of the flower budding promoting agent.

As one aspect of the flower budding promoting agent of the present invention, the α-ketol unsaturated fatty acid derivative (1) may also be used as is, but it may also be made into the various forms described below. In that case, if considering the above rule for administration of the α-ketol unsaturated fatty acid derivative (1), in general, inclusion in an amount of 0.1 to 100 ppm or so based upon the form, as a whole, is preferable. More preferably, it may be included in an amount of 1 to 50 ppm or so.

The α-ketol unsaturated fatty acid derivative (1), as explained above, may be used as is, as a flower budding promoting agent of the present invention, but it may also be made into a desired form able to be applied to the plant such as a liquid agent, solid agent, powder agent, emulsion agent, clinical additive etc. At that time, known carrier ingredients, preparation aids etc. pharmacologically able to be used depending upon the type of form may be suitably mixed in to an extent not detracting from the desired effect of the present invention, that is, the promotion of flower budding.

For example, as a carrier ingredient, when the flower budding promoting agent of the present invention is a clinical additive or a solid agent, in general talc, clay, vermiculite, diatom earth, kaolin, calcium carbonate, calcium hydroxide, white clay, silica gel and other inorganic substances or flour, starch or other solid carriers or when it is a liquid agent, in general water, xylene or other aromatic hydrocarbons, ethanol, ethylene glycol or other alcohols, acetone and other ketones, dioxane, tetrahydrofuran and other ethers, dimethyl formamide, dimethyl sulfoxide, acetonitrile and other liquid carriers may be used as the above carrier ingredients.

Further, as a preparation aid, for example, alkyl sulfuric acid esters, alkyl sulfonates, alkyl aryl sulfonates, dialkyl sulfonate succinates and other anionic surfactants, higher aliphatic amine salts and other cationic surfactants, polyoxyethylene glycol alkyl ethers, polyoxyethylene glycol acyl esters, polyoxyethylene glycol polyalcohol acyl esters, cellulose derivatives and other non-ionic surfactants, gelatin, casein, gum Arabic and other thickners, extending agents and binding agents and the like can be appropriately formulated.

Furthermore, according to need, a plant growth regulator, benzoic acid, nicotinic acid, nicotinic acid amide, pipecolinic acid or the like can be mixed in the flower budding promoter of the present invention to an extent not detracting from the desired effect of the present invention.

The above flower budding promoting agent of the present invention can be used for a variety of plants in various forms of use in accordance with its form.

For example, in the present invention, not only the growth points of the plant for blooming, but also the stalk, leaves and other parts of the plant or the entire plant may be treated with a liquid agent or emulsion agent by spraying, dripping, coating and the like or may be treated with a solid agent or powder agent by being made to absorb the agent from the ground into the roots.

Further, when the plant for promotion of blooming is water plants such as Lemnaceae or another water plant, it is also possible to treat it by being made to absorb the clinical additive from the roots or treated by a solid agent by gradually dissolving in water.

Further, the fatty acid derivative (1) of the present invention may be reacted with catechol amine such as dopamine or norepinephrine, then used as a flower budding promoting agent.

In that case, the ratio of the fatty acid derivative (1) of the present invention and the catechol amine may be suitably adjusted depending upon the objective and further depending upon the properties of the plant covered by the use and the specific aspect of the fatty acid derivative of the present invention. It is not specifically limited.

In addition, the frequency of administration of the flower budding promoter of the present invention to the plant is basically just once, whereby the desired effect can be obtained, but differs according to the type of the plant specimen, the purpose of administration, etc. When necessary, of course it may be administered a plurality of times. In that case, it is efficient to space the administrations by one week or more.

Furthermore, it is often effective to administer the flower budding promoting agent of the present invention, while treating the plant covered by the use of this depending upon with its properties.

For example, in the case of morning glory in the examples explained later, it is effective to use the flower budding promoting agent of the present invention, while keeping the plant in the dark for a certain period.

The type of the plant covered by the use of the flower budding promoting agent of the present invention is not particularly limited, but the invention is effective with both dicotyledons and monocotyledons.

Among angiosperms, as dicotyledons, for example plants of the genus *Pharbitis* (morning glory), plants of the genus *Caslystegia* (*C. japonica, C. hederacea, C. soldanella*), plants of the genus *Ipomoea* (*I. pes-caprae, I. batatas*), plants of the genus *Cuscuta* (*C. japonica, C. australis*) included in the Calystegia family; plants of the genus *Casuarinaceae*, plants of the genus *Stellaria*, plants of the genus *Caryophyllaceae*, plants of the genus *Cerastium*, plants of the genus *Spergularia*, plants of the genus *Arenaria*, plants of the genus *Moehringia*, plants of the genus *Pseudostellaria*, plants of the genus *Honkenya*, plants of the genus *Spergula*, plants of the genus *Spergularia*, plants of the genus *Silene*, plants of the genus *Choripetalae*, plants of the genus *Melandryum*, plants of the genus *Cucubalus*, and other plants of the Caryophyllaceae; plants of the Casuarinaceae family; plants of the Saururaceae family; plants of the Piperaceae family; plants of the Chloranthus family; plants of the Salicaceae family; plants of the Myricaceae family; plants of the Juglans family; plants of the Betulaceae family; plants of the Fagaceae family; plants of the Ulmaceae family; plants of the Moraceae family; plants of the Boehmeria family; plants of the Podostemaceae family; plants of the Proteaceae family; plants of the Olacaceae family; and plants of the Santalaceae family may be mentioned.

In addition, plants of the Viscum family, plants of the Asarum family, plants of the Mitrastemon family, plants of the Balanophora family, plants of the Polygonum family, plants of the Salsola family, plants of the Portulaca family, plants of the Mirabilis family, plants of the Theligonum family, plants of the Phytolacca family, plants of the Tetragonia family, plants of the Portulaca family, plants of the Magnoliaceae family, plants of the Trochodendoraceae family, plants of the Cercidiphyllaceae family, plants of the Nymphaeaceae family, plants of the Ceratopyllacea family, plants of the Ranunculus family, plants of the Lardizabalaceae family, plants of the Berberidaceae family, plants of the Cocculus family, plants of the Chimonanthus family, plants of the Lauraceae family, plants of the Meconopsis family, plants of the Cleome family, plants of the Brassica family, plants of the Drosera family, plants of the Nepenthes family, plants of the Kalanchoe family, plants of the Saxifraga family, plants of the Pittosporaceae family, plants of the Hamamelis family, plants of the Platanaceae family, plants of the Rosaceae family, plants of the Trifolium family, plants of the Oxalis family, plants of the Pelargonium family, plants of the Linum family, plants of the Zygophyllaceae family, plants of the Rutaceae family, plants of the Simaroubaceae family, plants of the Meliaceae family, plants of the Polygalaceae family, plants of the Euphorbia family, and plants of the Callitriche family may be illustrated.

Furthermore, the plants of the Buxaceae family, plants of the Empetraceae family, plants of the Coriariaceae family, plants of the Anacardiaceae family, plants of the Aquifoliaceae family, plants of the Celastraceae family, plants of the Staphyleaceae family, plants of the Icacinaceae family, plants of the Aceraceae family, plants of the Aesculus family, plants of the Sapindaceae family, plants of the Sabiaceae family, plants of the Impatiens family, plants of the Rhamnaceae family, plants of the Vitaceae family, plants of the Elaeocarpaceae family, plants of the Tiliaceae family, plants of the Abelmoschus family, plants of the Sterculiaceae family, plants of the Actinidiaceae family, plants of the Theaceae family, plants of the Hypericaceae family, plants of the Elatinaceae family, plants of the Tamarix family, plants of the Violaceae family, plants of the Flacourtiaceae family, plants of the Stachyuraceae family, plants of the Passifloraceae family, plants of the Begoniaceae family, plants of the Cactaceae family, plants of the Thymelaeaceae family, plants of the Elaeagnaceae family, plants of the Lythraceae family, plants of the Punicaceae family, plants of the Rhizophoraceae family, plants of the Alangiaceae family, plants of the Melastomataceae family, plants of the Trapaceae family, plants of the Onagraceae family, plants of the Haloragaceae family, plants of the Veronicaceae family, plants of the Araliaceae family, and plants of the Umbelliferae family may be illustrated.

Further, in addition to these, plants of the Cornaceae family, plants of the Diapensiaceae family, plants of the Clethraceae family, plants of the Pyrolaceae family, plants of the Ericaceae family, plants of the Myrsinaceae family, plants of the Primulaceae family, plants of the Plumbaginaceae family, plants of the Ebenaceae family, plants of the Symplocaceae family, plants of the Styracaceae family, plants of the Oleaceae family, plants of the Buddlejaceae family, plants of the Gentianaceae family, plants of the Apocynaceae family, plants of the Asclepiadaceae family, plants of the Polemoniaceae family, plants of the Boraginaceae family, plants of the Verbenaceae family, plants of the Labiatae family, plants of the Solanaceae (eggplant, tomato, and the like) family, plants of the Scrophulariaceae family, plants of the Bignoniaceae family, plants of the Pedaliaceae family, plants of the Orobanchaceae family, plants of the Geseneriaceae family, plants of the Lentibulariaceae family, plants of the Acanthaceae family, plants of the Myoporaceae family, plants of the Phrymaceae family, plants of the Plantaginaceae family, plants of the Rubiaceae family, plants of the Caprifoliaceae family, plants of the Adoxaceae family, plants of the Valerianaceae family, plants of the Dipsacaceae family, plants of the Cucurbitaceae family, plants of the Campanulaceae family, plants of the Compositae family, and the like may be illustrated.

Likewise, as monocotyledons, for example, plants of the family Lemnaceae included in plants of the genus *Lemnaceae* (*Lemnaceae*) and plants of the genus *Lemna* (*L. perpusilla, L. trisulca*), plants of the genus *Cattleya*, plants of the genus *Cymbidium*, plants of the genus *Dendrobium*, plants of the genus *Phalaenopsis*, plants of the genus *Vanda*, plants of the genus *Paphiopedilum*, and plants of the genus *Oncidiuma* including plants of the Spiranthes family, plants of the Typha family, plants of the Sparganium family, plants of the Potamogetonaceae family, plants of the Najadaceae family, plants of the Scheuchzeriaceae family, plants of the Alismataceae family, plants of the Hydrocharitaceae family, plants of the Triuridaceae family, plants of the Gramineae (rice, barley, wheat, rye, corn and the like) family, plants of the Cyperaceae family, plants of the Palmae family, plants of the Araceae family, plants of the Sparganiceae family, plants of the Commelinaceae family, plants of the Pontederiaceae family, plants of the Juncaceae family, plants of the Stemonaceae family, plants of the Liliaceae (asparagus and the like) family, plants of the Amaryllidaceae family, plants of the Dioscoreaceae family, plants of the Iridaceae family, plants of the Musaceae family, plants of the Zingiberaceae family, plants of the Cannaceae family, plants of the Burmanniaceae, and the like can be illustrated.

In the above, various aspects of utilizing of the compound of the present invention as a flower budding promoter were described specifically and in detail, but the compound of the present invention, as described above, may also be utilized a various plant activators such as a dormancy breaking agent, rooting agent, blooming promoter, flowering promoter, grass-stalk growth promoter, etc. In these cases as well, utilization is possible in the various ways in the same way as mentioned above.

EXAMPLES

As Examples, examples of production of the compounds according to the present invention and examples of use of the compounds will now be specifically described, but the present invention is not limited by these Examples in any way, but is specified by the description in the claims.

Further, the compound according to the present invention includes stereoisomers due to the plurality of asymmetrical carbons. The compound according to the present invention may be the individual optical isomers or their mixtures.

Production Example 1

Production of Specific α-Ketol Fatty Acid (2A)

In the following way, the specific ketol fatty acid (9-hydroxy-10-oxo-12(Z),15(Z)-octadecadienoic acid) having the formula (2A) was produced by the enzyme method.

1. Preparation of Rice Germ-Derived Lipoxygenase

Rice germ (350 g) was washed with petroleum ether, delipidated, and then dried. The resultant rice germ (250 g) was suspended in a 0.1 M acetate buffer solution (pH 4.5) (1.25 L), and the resultant suspension was homogenized.

Subsequently, the resultant homogenized extract was subjected to centrifugation at 16,000 rpm for 15 minutes, to thereby yield a supernatant (0.8 L).

Ammonium sulfate (140.8 g) (30% saturation) was added to the supernatant, and the resultant mixture was allowed to stand at 4° C. overnight.

Thereafter, the mixture was subjected to centrifugation at 9,500 rpm for 30 minutes, to thereby yield a supernatant (0.85 L). Ammonium sulfate (232 g) (70% saturation) was added to the supernatant, after which the resultant mixture was allowed to stand at 4° C. for five hours.

Subsequently, the mixture was subjected to centrifugation at 9,500 rpm for 30 minutes, to thereby yield a precipitate. The above-yielded precipitates (i.e., fractions obtained from the rice germ extract through addition of ammonium sulfate (30-70% saturation)) were dissolved in an acetate buffer solution (pH 4.5) (300 mL), and then heated at 63° C. for five minutes.

Thereafter, the precipitate was removed, and the supernatant was subjected to desalting through dialysis (3 L×3) by use of an RC dialysis tube (Pore 4, product of Spectrum: MWCO 12000-14000), to thereby yield a crude solution containing desired rice-germ-derived lipoxygenase.

2. Preparation of Flaxseed-Derived Allene Oxide Synthase

Acetone (250 mL) was added to flaxseeds (200 g) purchased from Ichimaru Pharcos Co., Ltd. The resultant mixture was homogenized (20 s×3), and the resultant precipitate was subjected to filtration by the use of a perforated plate funnel, to thereby remove the solvent.

Subsequently, the precipitate was again suspended in acetone (250 mL), and the suspension was homogenized (10 s×3), to thereby yield a precipitate.

The precipitate was washed with acetone and ethyl ether, and then dried, to thereby yield flaxseed powder (150 g).

The thus-yielded flaxseed powder (20 g) was suspended in a 50 mM phosphate buffer solution (pH 7.0) (400 mL) under cooling with ice. The resultant suspension was stirred by use of a stirrer at 4° C. for one hour to extraction.

The resultant extract was subjected to centrifugation at 11,000 rpm for 30 minutes. To the supernatant (380 mL) was added ammonium sulfate (105.3 g) (0-45% saturation), and the mixture was allowed to stand for one hour under cooling with ice. The mixture was further subjected to centrifugation at 11,000 rpm for 30 minutes, to thereby yield a precipitate. The precipitate was dissolved in a 50 mM phosphate buffer solution (pH 7.0) (150 mL), and the resultant solution was subjected to desalting through dialysis (3 L×3), to thereby yield a crude solution containing desired flaxseed-derived allene oxide synthase.

3. Preparation of α-Linolenic Acid Sodium Salt

α-Linolenic acid serving as a starting material has considerably low water solubility. Therefore, in order to cause α-linolenic acid to function effectively as an enzyme substrate, an α-linolenic acid sodium salt was prepared. Specifically, sodium carbonate (530 mg) was dissolved in purified water (10 mL), and then heated to 55° C. α-Linolenic acid (product of Nacalai Tesque, Inc.) (278 mg) was added dropwise to the resultant solution, and the mixture was stirred for three hours.

After completion of the reaction, the reaction mixture was neutralized with Dowex50W-X8 ($H^+$ form) (product of Dow Chemical Co.), to thereby yield a precipitate. The precipitate was subjected to filtration to thereby remove a resin. Subsequently, the precipitate was dissolved in MeOH, and then the solvent was removed under vacuum.

The thus-obtained product was recrystallized with isopropanol, to thereby yield a desired α-linolenic acid sodium salt (250 mg, 83%).

4. Production of Specific Ketol Fatty Acid (2A)

The α-linolenic acid sodium salt yielded above in 3 (15 mg: 50 μmol) was dissolved in a 0.1 M phosphate buffer solution (pH 7.0) (30 mL). To the resultant solution was added the rice-germ-derived lipoxygenase crude solution prepared above in 1 (3.18 mL) at 25° C. under oxygen flow, and the mixture was stirred for 30 minutes. The rice-germ-derived lipoxygenase crude solution (3.18 mL) was further added to the mixture, and the resultant mixture was stirred for 30 minutes.

After completion of the stirring, the allene oxide synthase crude solution prepared above in 2 (34.5 mL) was added to the lipoxygenase reaction mixture under nitrogen flow, and the resultant mixture was stirred for 30 minutes. Thereafter, dilute hydrochloric acid was added to the reaction mixture under cooling by use of ice, to thereby adjust the ph of the mixture to 3.0. Subsequently, the reaction mixture was subjected to extraction with a solvent mixture of $CHCl_3$:MeOH (10:1). The thus-obtained organic layer was subjected to dehydration through addition of magnesium sulfate, and the solvent was removed under vacuum and then dried.

The thus-obtained crude product was subjected to HPLC, and a fraction corresponding to the peak of specific α-ketol fatty acid (2A) (retention time: about 16 min) was obtained. Chloroform was added to the thus-obtained fraction, the separated chloroform layer was washed with water, and the chloroform was removed by use of an evaporator, to thereby yield a purified product.

In order to confirm the structure of the purified product, the product was subjected to measurement of $^1H$ and $^{13}C$-NMR spectra by use of a heavy methanol solution. As a result, in the $^1H$-NMR measurement, signals corresponding to an end methyl group [δ0.98 (t)], two sets of olefins [(δ5.25, 5.40), (δ5.55, 5.62)], a secondary hydroxyl group [δ4.09 (dd)] and numerous methylene groups were observed, and the product was presumed to be specific ketol fatty acid (2).

Furthermore, when comparing the $^{13}C$-NMR chemical shifts, the product matched the specific α-ketol fatty acid (2A) (see Japanese Patent Publication (A) No. 10-324602, page 7, column 11, line 1 from the bottom on, "Production Example (extraction method)", $^{13}C$-NMR chemical shifts (same publication, page 8, column 13, line 2 on, [0054] and (0055])

Thus, the synthesized product obtained by means of the above enzyme method was identified as 9-hydroxy-10-oxo-12(Z),15(Z)-octadecadienoic acid. That is, it became clear that said synthesized product is a compound of the general formula (2) in which $R_1$ is a $C_2$ straight chain alkyl group and $R_2$ is a $C_7$ straight chain saturated hydrocarbon chain, that is, an α-ketol fatty acid (2A).

Production Example 2

Production Example 1 of a Specific α-Ketol Fatty Acid Derivative (1A)

In the following way, the specific ketol fatty acid derivative 9,15,16-trihydroxy-10-oxo-12(Z)-octadecenoic acid (1A) was produced, isolated and purified, and structurally analyzed.

The specific ketol fatty acid (2A) (500 mg) was dissolved in 1.3 L of water. Chlorinated isocyanulic acid (192 mg) was added to this, then the mixture was stirred at 25° C. for 30 minutes for the reaction. This reaction solution was extracted by chloroform (500 mL, 3×), dried by anhydrous magnesium sulfate, and concentrated after being filtered. The obtained crude extract was confirmed to be the product (1A) by HPLC (column: CAPCELL PAK C-18 UG120, 4.6×250 mm (Shiseido), solvent: 25% acetonitrile+0.1% trifluoroacetic acid, flow rate: 1 mL/min, wavelength: 300 nm).

In regards to the 5.7 minute peak of the retention time, the column size was increased (CAPCELL PAK C-18 UG120, 10×250 mm) to collect the product, then the product was extracted by chloroform to obtain the compound (1A) (187.5 mg) (yield 38%). The compound (1A) was structurally analyzed.

The absorption spectrum was measured by a UV V-560 spectrophotometer (JASCO), while the $^1H$- and $^{13}C$-NMR were measured by an ECP-400 (JEOL). The results are as follows:

Compound (1A)

UV λmax (MeOH, m): 201.0 nm (ε=4520).

$^1H$-NMR (400 MHz, $CDCl_3$): δ0.97 (3H, t, J=7.2, 18-$H_3$), 1.25-1.46 (8H, 4, 5, 6, 7-$H_2$), 1.63 (4H, m, 3, 17-$H_2$), 1.63, 1.83 (both 1H, m, 8-$H_2$), 2.34 (2H, t-like, J=7.2, 2-$H_2$), 2.58, 2.66 (both 1H, m, 14-$H_2$), 3.31 (2H, m, 11-$H_2$), 3.75 (1H, m, 15-H), 3.85 (1H, m, 16-H), 4.24 (1H, m, 9-H), 5.68 (1H, m, 12-H), 5.72 (1H, m, 13-H).

$^{13}C$-NMR (100 MHz, $CDCl_3$): 10.0 (C-18), 24.5, 27.8, 28.1, 28.8, 28.9, 29.0 (C-3, 4, 5, 6, 7, 17), 33.5 (C-2), 33.8 (C-8), 33.9 (C-14), 36.6 (C-11), 66.1 (C-15), 73.9 (C-16), 76.2 (C-9), 123.3 (C-13), 128.9 (C-12), 179.1 (C-1), 210.3 (C-10).

The protons and carbons were assigned by measuring the DIFCOSY, HMQC, and HMBC spectra and other 2-dimensional NMR spectra. The obtained data was compared with the data of the compound (2A) [described in Japanese Patent Publication (A) No. 9-295908 and the document (Yokoyama et al., Plant Cell Physiol., 41, 110-113, 2000)], whereupon one olefin group of the compound (2A) disappeared and instead two methylenes with hydroxyl groups bound to them were recognized.

The disappeared olefin was judged to be at the 15-position by the results of analysis of HMBC and DIFCOSY.

From the above, the positions of the methines with hydroxyl groups bonded to them were determined to be C-15 and C-16. Note that a 9-position hydroxyl group and a 10-position oxo group were present.

By the above data, the structure of the compound (1A) was determined to be that of the formula (1A).

Production Example 3

Production Example 2 of Specific α-Ketol Fatty Acid Derivative (1A)

In the following way, the optimal ratio of chemicals when producing the specific ketol fatty acid derivative 9,15,16-trihydroxy-10-oxo-12(Z)-octadecenoic acid (1A) using sodium hypochlorite was investigated.

An ethanol solution (112 mM, 3.5%) of the specific α-ketol fatty acid (2A) (188 μl) was added to purified water (25 mL) (did not entirely dissolved, remained in white turbid state). While stirring this aqueous solution of the specific α-ketol fatty acid (2A), increased amount of a sodium hypochlorite solution (Wako Pure Chemical Industries) was added, from 6 μl, by 1 μl at a time to 20 μl.

10 minutes after this addition, the mixture was analyzed by HPLC (column: CAPCELL PAK C-18 UG120, 4.6×250 mm, solvent: 25% acetonitrile+0.1% trifluoroacetic acid, flow rate: 1 ml/min, wavelength: 300 nm) and the rate of production of the specific α-ketol fatty acid derivative (1A) was measured.

Figure 1:
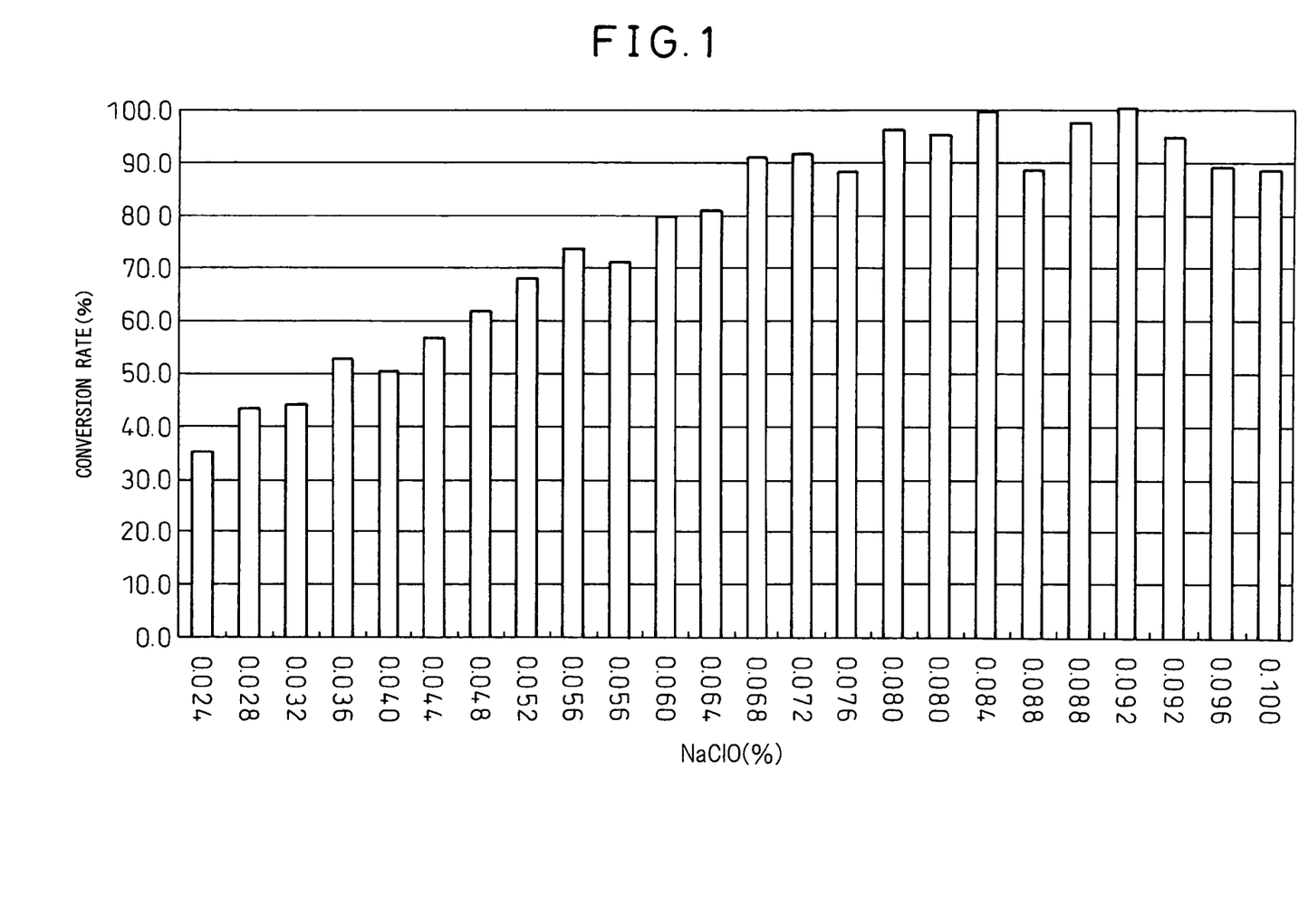
FIG. 1 is a graph showing the transformation ratio from a specific α-ketol fatty acid (1A) of a specific α-ketol fatty acid derivative (1A)

As a result, it was learned that when adding the sodium hypochlorite solution to give 0.09% or so, nearly 100% of the specific α-ketol fatty acid (2A) was transformed to the specific α-ketol fatty acid derivative (1A). The results are shown in FIG. 1.

Production Example 4

Production Example 3 of Specific α-Ketol Fatty Acid Derivative (1A)

The specific ketol fatty acid (2A) (500 mg) was dissolved in 1.9 L of water. A sodium hypochlorite solution (1.2 mL) was added thereto, then the mixture was allowed to stand at room temperature for 10 minutes or more.

The reaction solution was extracted by chloroform (500 mL, 3×), dried by anhydrous magnesium sulfate, filtered, then concentrated. The obtained crude extract was further fractionated by HPLC (column: CAPCELL PAK C-18 UG120, 10×250 mm, solvent: 25% acetonitrile+0.1% trifluoroacetic acid, flow rate: 4 ml/min, wavelength: 300 nm).

The product was obtained, then extracted by chloroform to obtain the compound (1A) (472 mg) (yield 85%).

Usage Example

Activity of Specific α-Ketol Fatty Acid Derivative (1A) in Increasing Flower Budding of Morning Glory Seeds of morning glory (variety: murasaki) (9 g) were subjected to concentrated sulfuric acid treatment for 20 minutes, and then allowed to stand under water flow overnight.

Subsequently, the seeds were placed on wet sea sand such that the emerging sites of the roots were directed upward for 24 hours, to thereby produce roots. The seeds having roots were planted in sea sand at a position 1 cm below the surface of the sand, and then cultured under continuous light irradiation (for about five days).

The entire plant bodies of the morning glory having leaves produced through this culture were transferred into a culture solution KNO$_3$(250 mg), NH$_4$NO$_3$ (250 mg), KH$_2$PO$_4$ (250 mg), MgSO$_4$.7H$_2$O (250 mg), MnSO$_4$.4H$_2$O (1 mg), Fe-citrate n-hydrate (6 mg), H$_3$BO$_3$ (2 mg), CuSO$_4$.5H$_2$O (0.1 mg), ZnSO$_4$.7H$_2$O (0.2 mg), Na$_2$MoO$_4$.2H$_2$O (0.2 mg), Ca(H$_2$PO$_4$)$_2$.2H$_2$O (250 mg) in distilled water (1,000 mL)].

Water or a 0.01, 0.1, 1 or 100 μM specific α-ketol fatty acid (1A) aqueous solution was sprayed to the cultured system in an amount of 0.1 mL/plant, then the plants were treated by darkness (for 13.5 hours).

Thereafter, the morning glory was grown under continuous light irradiation at 25° C. for 14 days, and on the 14th day the number of the flower buds was measured.

The results of eight specimens of morning glory were averaged. The result is shown in FIG. 2.

The number of flower buds formed when spraying water was an average of 1.25 buds/plant.

Figure 2:
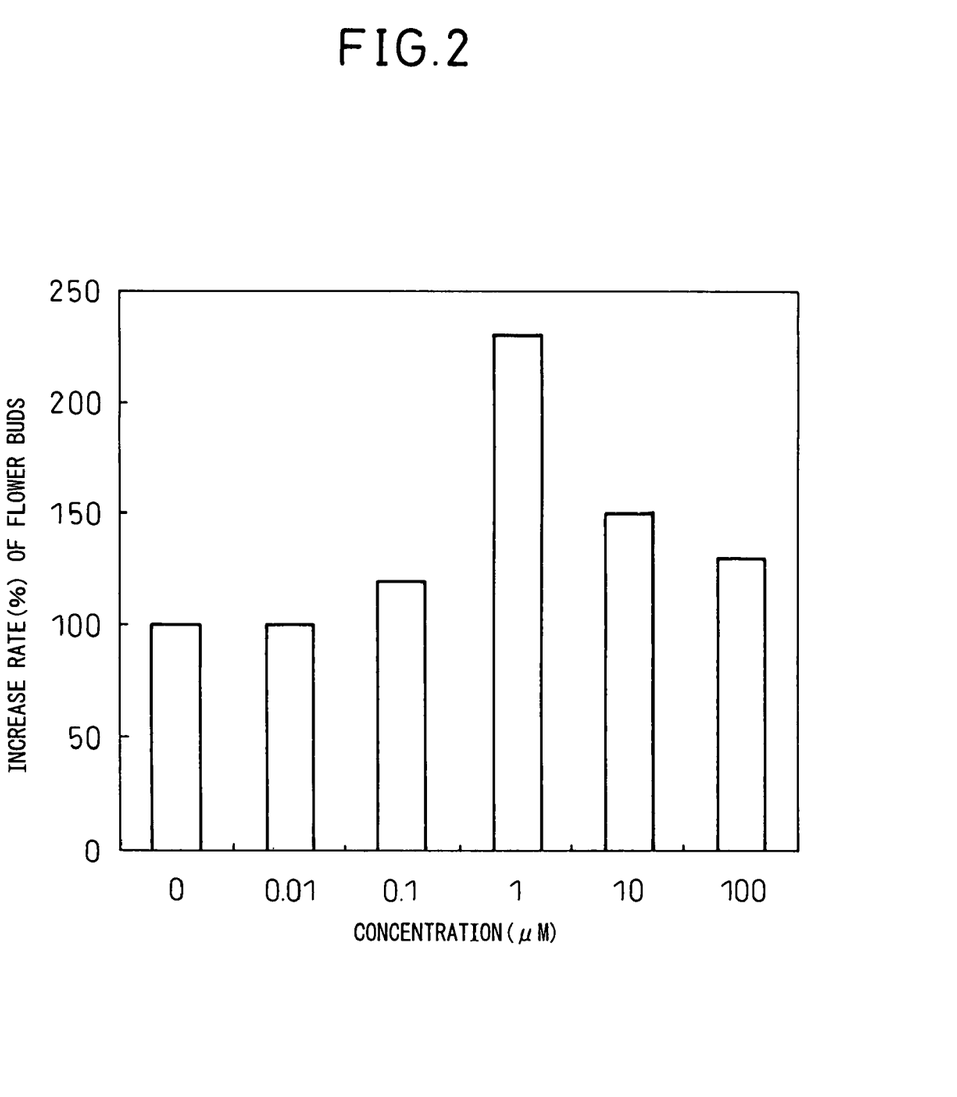
FIG. 2 is a graph showing the activity of the specific α-ketol fatty acid derivative (1A) in increasing flower buds for morning glory.

As shown in FIG. 2, the number of flower buds formed by the specific α-ketol fatty acid derivative (1A) increased by 200% or more.

The optimum concentration was 1 μM. This is a concentration of 1/100 the optimum concentration 100 μM of the specific α-ketol fatty acid (2A) (see Japanese Patent Publication (A) No. 11-29410).

Evaluation of Stability: Stability of Specific α-Ketol Fatty Acid Derivative (1A)

The stability of the specific α-ketol fatty acid derivative (1A) was evaluated as follows.

A 16 mM ethanol solution of the derivative (1A) was diluted by water 30-fold. This diluted solution was allowed to stand for an extended period at each of the temperatures of 4° C., 25° C. and 50° C. The extent of decomposition over time was analyzed by HPLC (column: CAPCELL PAK C-18 UG120, 4.6×250 mm, solvent: 50% acetonitrile+0.1% trifluoroacetic acid, flow rate: 1 ml/min, wavelength: 210 nm).

For comparison, a solution prepared by similarly diluting the specific α-ketol fatty acid derivative (2A) was allowed to stand for an extended period at each of 25° C. and 50° C. The extent of decomposition was similarly investigated.

Figure 3:
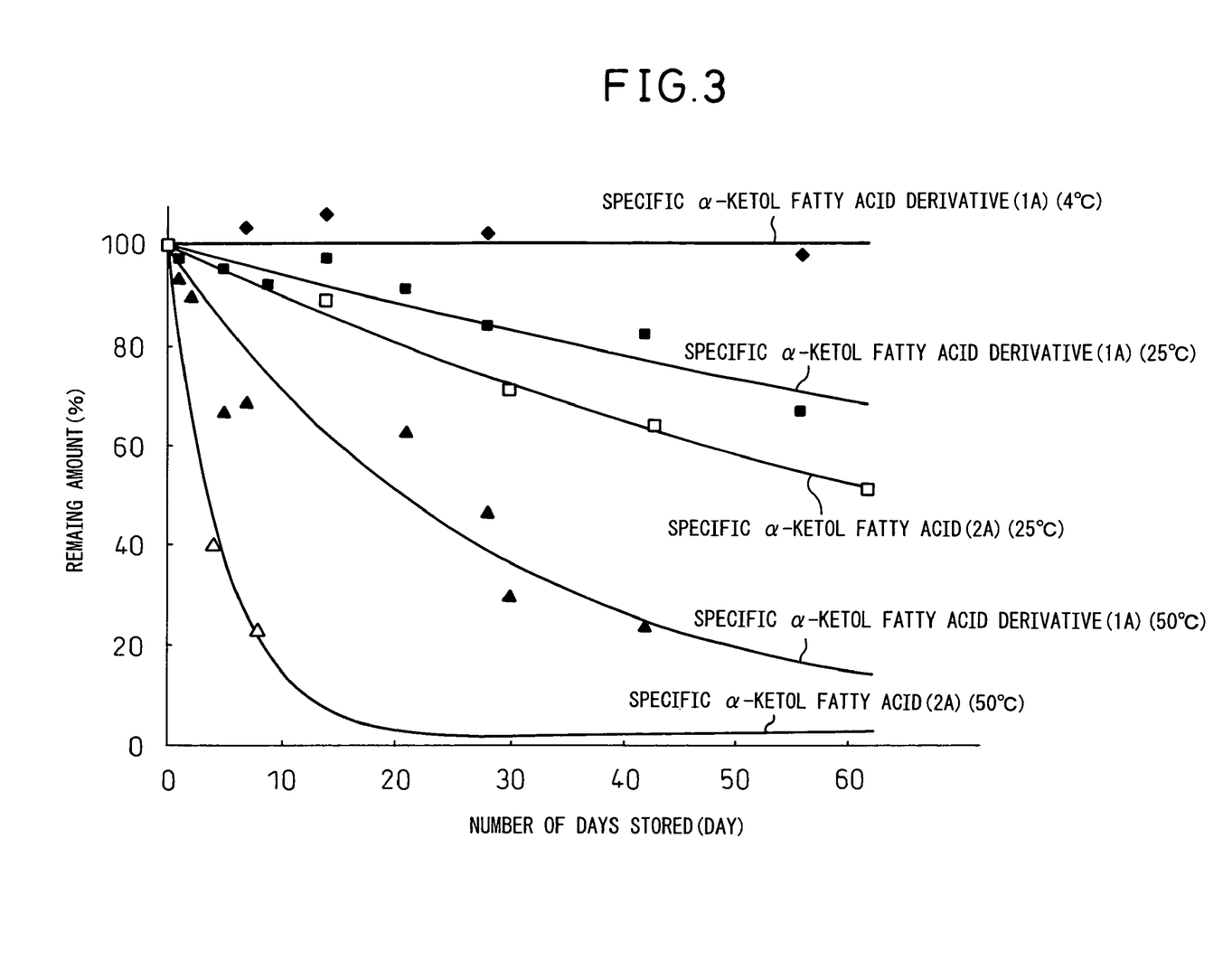
FIG. 3 is a graph showing the results of a test for evaluating the stability of the specific α-ketol fatty acid derivative (1A) and a specific α-ketol fatty acid (2A).

The results of investigation are shown FIG. 3. From the results of FIG. 3, it is clear that the specific α-ketol fatty acid derivative (1A) of the present invention is superior in stability to the specific α-ketol fatty acid derivative (2A) of the comparison at both the temperatures of 25° C. and 50° C.

Further, the stability at 4° C. was investigated only for the specific α-ketol fatty acid derivative (1A) of the present invention, but according to the results, when compared with 25° C. and 50° C., the derivative was far superior in stability.

The invention claimed is:

1. An α-ketol unsaturated fatty acid derivative represented by the formula (1):

Formula (1)

wherein R$_1$ indicates a C$_1$ to C$_5$ straight chain alkyl group or C$_3$ to C$_5$ straight chain unsaturated hydrocarbon group having one or two double bonds, R$_2$ indicates a C$_1$ to C$_{15}$ straight chain alkylene or C$_2$ to C$_{15}$ straight chain unsaturated hydrocarbon chain having one to three double bonds, provided that the maximum number of double bonds between carbons is 4.

2. A plant growth regulating agent comprising an α-ketol unsaturated fatty acid derivative represented by the formula (1):

Formula (1)

wherein R$_1$ indicates a C$_1$ to C$_5$ straight chain alkyl group or C$_3$ to C$_5$ straight chain unsaturated hydrocarbon group having one or two double bonds, R$_2$ indicates a C$_1$ to C$_{15}$ straight chain alkylene or C$_2$ to C$_{15}$ straight chain unsaturated hydrocarbon chain having one to three double bonds, provided that the maximum number of double bonds between carbons is 4.

3. A plant growth regulating agent as claimed in claim 2, wherein said unsaturated fatty acid derivative has 18 carbon atoms and has one or two double bonds between the carbons.

4. A plant growth regulator as claimed in claim 2 wherein said unsaturated fatty acid derivative is 9,15,16-trihydroxy-10-oxo-12(Z)-octadecenoic acid.

5. A plant growth regulator as claimed in claim 3 wherein said unsaturated fatty acid derivative is 9,15,16-trihydroxy-10-oxo-12(Z)-octadecenoic acid.

* * * * *